(12) United States Patent
Powell et al.

(10) Patent No.: US 9,668,669 B2
(45) Date of Patent: Jun. 6, 2017

(54) SYSTEMS, METHODS AND DEVICES FOR SENSING EMG ACTIVITY

(71) Applicant: POWELL MANSFIELD, INC., San Diego, CA (US)

(72) Inventors: Nelson Powell, Atherton, CA (US); Perry Thomas Mansfield, Coronado, CA (US)

(73) Assignee: POWELL MANSFIELD, INC., San Diego, CA (US)

( * ) Notice: Subject to any disclaimer, the term of this patent is extended or adjusted under 35 U.S.C. 154(b) by 0 days.

(21) Appl. No.: 14/903,561

(22) PCT Filed: Feb. 27, 2015

(86) PCT No.: PCT/US2015/018196
§ 371 (c)(1),
(2) Date: Jan. 7, 2016

(87) PCT Pub. No.: WO2015/131159
PCT Pub. Date: Sep. 3, 2015

(65) Prior Publication Data
US 2016/0150993 A1    Jun. 2, 2016

Related U.S. Application Data

(60) Provisional application No. 61/946,259, filed on Feb. 28, 2014.

(51) Int. Cl.
*A61B 5/04*    (2006.01)
*A61B 5/0488*  (2006.01)
(Continued)

(52) U.S. Cl.
CPC .............. *A61B 5/0488* (2013.01); *A61B 5/01* (2013.01); *A61B 5/04012* (2013.01);
(Continued)

(58) Field of Classification Search
CPC .. A61B 5/0488; A61B 5/0492; A61B 5/04882
(Continued)

(56) References Cited

U.S. PATENT DOCUMENTS

| | | | |
|---|---|---|---|
| 4,807,643 A * | 2/1989 | Rosier | A61B 5/05 600/546 |
| 5,212,476 A | 5/1993 | Maloney | |

(Continued)

OTHER PUBLICATIONS

Friberg D. et al. "Histological Indications of a Progressive Snorer's Disease in an Upper Airway Muscle" Am J Respir Crit Care Med 1998; 157:586-593.
(Continued)

*Primary Examiner* — Daniel Cerioni
(74) *Attorney, Agent, or Firm* — Cooley LLP

(57) ABSTRACT

Some embodiments of the present disclosure are directed to methods, systems and probe devices for detecting EMG activity. In some embodiments, such methods, systems and devices are used in aiding the diagnosis of Obstruction Sleep Apnea (OSA). In some embodiments, a probe is provided and comprises an elongated member configured with a size and shape for placement adjacent at least one of the soft palate and pharyngeal wall of the patient after insertion of the probe into the patient. The probe may also include at least one sensor configured to sense at least EMG activity of muscle layers of at least one of the soft palate and pharyngeal wall and output sensor signals corresponding thereto.

21 Claims, 7 Drawing Sheets

(51) Int. Cl.
*A61B 5/00* (2006.01)
*A61B 5/01* (2006.01)

(52) U.S. Cl.
CPC ............ *A61B 5/4818* (2013.01); *A61B 5/682* (2013.01); *A61B 5/04886* (2013.01); *A61B 2562/046* (2013.01)

(58) Field of Classification Search
USPC ........................................................ 600/546
See application file for complete search history.

(56) References Cited

U.S. PATENT DOCUMENTS

| | | | | |
|---|---|---|---|---|
| 5,449,381 | A * | 9/1995 | Imran | A61N 1/3956 607/122 |
| 5,546,952 | A | 8/1996 | Erickson | |
| 6,334,068 | B1 * | 12/2001 | Hacker | A61B 5/0488 128/901 |
| 6,361,494 | B1 | 3/2002 | Lindenthaler | |
| 6,597,944 | B1 | 7/2003 | Hadas | |
| 7,942,824 | B1 * | 5/2011 | Kayyali | A61B 5/021 128/204.23 |
| 8,597,183 | B2 | 12/2013 | Addington et al. | |
| 2005/0159659 | A1 | 7/2005 | Sawan et al. | |
| 2007/0074728 | A1 | 4/2007 | Rea | |
| 2007/0173893 | A1 * | 7/2007 | Pitts | A61N 1/36017 607/2 |
| 2010/0137736 | A1 * | 6/2010 | Addington | A61B 5/202 600/546 |
| 2011/0093032 | A1 * | 4/2011 | Boggs, II | A61B 5/415 607/42 |
| 2013/0150749 | A1 | 6/2013 | McLean et al. | |
| 2014/0135868 | A1 * | 5/2014 | Bashyam | A61N 1/3601 607/42 |

OTHER PUBLICATIONS

Woodson B. Tucker et al. "Histopathologic Changes in Snoring and Obstructive Sleep Apnea Syndrome" Laryngoscope 101: Dec. 1991, pp. 1318-1322.

Namysłwski G. et al. "Histopathologic Changes of the Soft Palate in Snoring and Obstructive Sleep Apnea Syndrome Patients" Otolaryngol Pol. 2005; 59(1):13-9.

Paulson, Friedrich P. et al. "Upper Airway Epithelial Structural Changes in Obstructive Sleep-disoriented Breathing" Am Journal of Respiratory and Critical Care Medicine, vol. 166, 2002, pp. 501-509.

Wasserman DE et al. "Industrial vibration—an overview" J Am Soc Saf Eng Jun. 1974; 19(6):38-43.

Curry Brian D. et al. "Vibration injury damages arterial endothelial cells" Muscle Nerve 25, Feb. 19, 2002, 527-34.

Govindaraju et al. "Comparison of continuous and intermittent vibration effects on rat-tail artery and nerve" Muscle Nerve Aug. 2006; 34(2): 197-204.

Powell, Nelson B. et al. "Patterns in pharyngeal airflow associated with sleep-disorder breathing" Sleep Medicine 12 (2011), pp. 966-974.

Young, Terry et al. "The Occurrence of Sleep-Disordered Breathing Among Middle-Aged Adults" The New England Journal of Medicine, Apr. 29, 1993; vol. 328, No. 17, pp. 1230-1235.

Lee, Sharon A. et al. "Heavy Snoring as a Cause of Carotid Artery Atherosclerosis" SLEEP, vol. 31, No. 9, 2008, pp. 1207-1213.

Cho, Jin-Gun et al. Tissue Vibration Induces Carotid Artery Endothelial Dysfunction: A Mechanism Linking Snoring and Carotid Atherosclerosis? SLEEP 2011, vol. 34, No. 6, pp. 751-757.

Amatoury J. et al. "Snoring-related energy transmission to the carotid artery in rabbits" J Appl Physiol 100:1547-1553, Feb. 2, 2006.

Guilleminault, C. et al. "Is obstructive sleep apnea syndrome a neurological disorder? A continuous positive airway pressure follow-up study" Ann Neurol. Dec. 2005; 58(6):880-7.

Dematteis, M. "A simple procedure for measuring pharyngeal sensitivity: a contribution to the diagnosis of sleep apnea" Thorax 2005;60:418-426.

Kimoff R. John et al. "Upper Airway Sensation in Snoring and Obstructive Sleep Apnea" Am J Respir Crit Care Med, vol. 164, pp. 250-255, 2001.

Salerno, F. G. et al. "Airway inflammation in patients affected by obstructive sleep apnea syndrome" Respiratory Medicine 2004, 98, 25-28.

Thomas B. Rice et al., "A Nuisance or Nemesis: The adverse Effects of Snoring" SLEEP 2011, vol. 34, No. 6, pp. 693-694.

R. Sabato et al., "Airway Inflammation in Patients Affecetd by Obstructive Sleep Apnea" Monaldi Arch Chest Dis 2006; 65: 2, 102-105.

International Search Report and Written Opinion, mailed Jun. 8, 2015, for International Application No. PCT/US2015/018196.

Chen et al. "The feasibility and reliability of using circular electrode for sphincter of Oddi electromyography in anaesthetised rabbits" Neurogastroenterol Motil (2009) 21, 651-e29.

Anton van Boxtel "Facial EMG as a Tool for Inferring Affective States" Proceedings of Measuring Behavior 2010 (Eindhoven, The Netherlands, Aug. 24-27, 2010), pp. 104-108.

Yoshida, et al. "Clinical Science: EMG Approach to Assessing Tongue Activity Using Miniature Surface Electrodes" Journal of Dental Research, 61 (10): 1148-1152, Oct. 1982.

Katz, Eliot S. et al. "Genioglossus Activity in Children with Obstructive Sleep Apnea during Wakefulness and Sleep Onset" Am. J. Respir. Crit. Care. Med., vol. 168, pp. 664-670, 2003 (originally published in Press as DOI: 10.1164/rccm.200301-092OC on Jul. 11, 2003).

Katz, Eliot S. et al. "Genioglossus Activity During Sleep in Normal Control Subjects and Children with Obstructive Sleep Apnea" Am. J. Respir. Crit. Care. Med., vol. 170, pp. 553-560, 2004 (originally published in Press as DOI: 10.1164/rccm.200403-262OC on Jun. 1, 2004).

Milidonis, Mary K. et al. "Surface intraoral genioglossus EMG recording technique for kinesiologic studies" Am. J. Orthod. Dentofac. Orthop., vol. 94, No. 3, pp. 240-244, Sep. 1988.

* cited by examiner

SYSTEMS, METHODS AND DEVICES FOR SENSING EMG ACTIVITY

CROSS-REFERENCE TO RELATED APPLICATIONS

This application is a 371 National Stage application of PCT/US2015/018196, filed Feb. 27, 2015, entitled "Systems, Methods and Devices for Sensing EMG Activity", and which claims benefit of and priority under 35 USC §119 to U.S. Provisional Patent Application Ser. No. 61/946,259 filed Feb. 28, 2014, entitled "Systems, Methods and Devices for Sleep Apnea," the entire contents of each application is incorporated by reference herein in its entirety.

FIELD OF THE DISCLOSURE

Embodiments of the current disclosure are directed toward sensing EMG activity, and more particularly, systems, methods and devices for sensing EMG activity.

BACKGROUND OF THE INVENTION

Diagnosis and assessment of various physiological conditions such as obstructive sleep apnea (OSA), hearing loss, vascular diseases, urological conditions, etc., can be accomplished by way of evaluation of muscles, cavities, etc., that are part of the tissues/organs associated with the physiological conditions. For example, snoring, a form of OSA, can be the result of the dysfunction of muscular and nerve tissues in the pharyngeal airway. Another example is valvular disease which involves damages or defects to one or more of the four valves of the heart. These are just two of the myriad conditions that can be diagnosed and analyzed by studying the associated muscles, tissues, valves, etc.

OSA, a collective term used for conditions that over time cause damage to the delicate soft tissues of the upper airway from turbulent snoring, can comprise anatomically obstructive processes that result in nocturnal narrowing of the upper airway leading to partial or complete obstruction of the airway. The upper airway encompasses the entire upper airway passages to include the nasal cavity, oropharynx and hypo pharynx. Partial and total airway obstruction results in sleep arousals, sleep fragmentation and subsequent behavioral derangements such as excessive daytime sleepiness. Concurrently, pathophysiologic derangements usually accompany the behavioral decrements with altered daytime performance and excessive daytime sleepiness. The cardiovascular derangements can cause in part high blood pressure, stroke, myocardial infarction and death. Decreased quality of life and a shortened life span are common in subjects with untreated OSA.

Snoring is a common finding and afflicts approximately 40% of the adult population. One of the causes of snoring is the narrowing of the airway during sleep and is the result of turbulent airflow vibrations along soft tissues of the upper airway during inspiration and expiration. Snoring also results from dysfunction of the muscular and nerve tissues in the pharyngeal airway. Such dysfunctions may have many origins, examples of which include an extreme air pressure and airflow turbulences that cause constant degradations of muscle and subsequent neural damage along the upper airway. Further, turbulent upper airway airflow can be causal to the development of obstructive sleep apnea. It is generally understood that a major causal mechanism for sleep apnea is narrowing along upper airway structure from the nose, palate, lateral pharyngeal wall and tongue base. Poor quality of the palatal tissues and nerves, an issue that is more difficult to treat, can be another cause of sleep apnea.

Snoring is a medical sign of nocturnal partial airway obstruction and when snoring is chronic (e.g., every night) the subject can have an about 80% risk of obstructive sleep apnea (OSA). The prevalence of OSA has been reported in peer reviewed literature using epidemiologic evidence based medicine to be about 24% in males and about 9% of women in the age grouping of 30-60 years of age. It is well established that chronic snoring and OSA are associated with two major pathologic problems. The first is behavioral derangements secondary to abnormal sleep patterns. This is caused by nocturnal airway collapse and subsequent arousals in sleep stages and resultant sleep fragmentation. Subjects may experience on awakening excessive daytime sleepiness (EDS) with a constellation of symptoms such as morning headaches, lethargy, irritability, memory loss and an overall visceral effect on well-being. They can be at risk for unintended sleep periods which may lead to catastrophic accidents or even death (e.g., if they occur during driving).

The second problem is pathophysiologic derangements. These are caused by a lack of oxygen along with sympathetic nervous system activation that is so stressful on an about nightly basis that the subjects are at significant risk for cardiovascular disease (heart attack, high blood pressure, stroke and sudden death during sleep). Furthermore, repetitive oxygen desaturation has now been reported to cause permanent brain damage over time and many of the subjects with OSA are at risk for this finding. The overall outcomes of snoring and/or OSA are a premature shortening of life span. All of these conditions are secondary to damaged soft tissues in the upper airway that collapses during sleep in varied degrees and severity depending on the amount of soft tissue excess and floppiness.

SUMMARY OF SOME OF THE EMBODIMENTS

Embodiments of a system and a method for aiding in the diagnosis of a condition of a patient are provided herein. In some embodiments, the system may comprise at least one sensor configured for placement on the surface of tissue of a patient at a first location and configured to produce first signals responsive to at least EMG activity of at least one muscle and/or muscle layer proximate the first location. In some embodiments, the method may comprise the steps of providing the probe; analyzing the first signals, and determining whether the first signals correspond to EMG activity of the at least one muscle and/or muscle layer.

An example of the at least one sensor can be a bipolar surface electrode (e.g., spherical electrode). In some embodiments, the surface of the tissue may be mucosal. In some embodiments, the first signals comprise spontaneous EMG activity including fibrillation potentials, positive sharp waves, complex repetitive discharges, fasciculation potentials, myokymic discharges, and/or the like. In some embodiments, the first signals comprise motor unit potentials (MUP's). In some embodiments, the system may also include a probe having positioned thereon the at least one sensor and being configured with a size and shape to effect placement of the at least one sensor at the first location such that the sensor can detect EMG activity of the at least one muscle. It may also comprise a processor having computer instructions operational thereon configured for causing the processor to execute the steps of the methods of some of the embodiments herein. For example, the methods may comprise the steps of analyzing the first signals, and determining whether the first signals correspond to EMG activity of the at least one muscle and/or muscle layer. Further, the methods may comprise diagnosing a condition of the patient based upon the determined EMG activity, wherein the determined EMG activity corresponds to spontaneous EMG activity and/or MUP's with various abnormal parameters of the at least one muscle. In some embodiments, determining spontaneous activity comprises determining whether the first signals comprise at least one of fibrillation potentials, positive sharp waves, complex repetitive discharges, fasciculation potentials, and myokymic discharges. In some embodiments, determining abnormal MUP's comprises evaluating one or more parameters of MUPs of the determined EMG activity for deviations from MUP benchmarks that indicate normal MUPs. Further, the instructions may be configured to cause the processor, upon a determination of EMG activity, to grade the EMG activity, wherein grading comprises determining one or more periods of occurrence of the spontaneous EMG activity or abnormal MUP's. The periods may comprise at least one of rare, occasional, frequent and abundant. In some embodiments, for abnormal MUP's, the grading may comprise evaluating one or more parameters of some or all characteristics of the MUP's. For example, the characteristics may comprise MUP parameters of the MUPs such as but not limited to size, shape, complexity, amplitude, phase, duration, area, and/or the like, and grading the EMG activity may comprise evaluating (e.g., measuring) the parameters. Grades may be based on measures of the parameter, for example, indicating the severity, frequency of occurrence, etc., of the abnormal MUP's. For example, an MUP with oversized amplitude may be identified as abnormal, and the size of the amplitude may determine if the abnormality can be ranked or graded as light, medium, large, severe, etc.

In some embodiments of the disclosure herein, the method for aiding in the diagnosis of a condition of a patient may comprise the steps of arranging a plurality of bipolar surface electrodes on the surface of mucosal tissue of a patient each at a predetermined location on tissue, each predetermined location plurality of locations, each location corresponding to a specific muscle and/or muscle layer, wherein each electrode configured to produce first signals responsive to spontaneous EMG activity or abnormal MUP's of the specific muscle/layer; determining whether the first signals of any of the electrodes correspond to spontaneous EMG activity or abnormal MUP's of respective muscles/layers; and determining whether the spontaneous EMG activity or abnormal MUP's of one or more muscles/layers are indicative of obstructive sleep apnea.

In some embodiments of the system and the methods disclosed herein, the size and shape of the probe are configured to position the at least one sensor proximate the muscle layers of at least one of the soft palate, pharyngeal wall, and tongue, and wherein the computer instructions are additionally configured to cause the processor to execute the step of differentiating EMG activity from EMG artifacts. The at least one sensor may comprise a plurality of sensors, wherein each sensor comprises a bipolar surface electrode. In some embodiments, the at least one sensor may include a thermal sensor. In some embodiments, of the plurality of sensors, each electrode may be spaced apart from an adjacent electrode by about 5 mm, or the spacing may be configured to correspond to the muscle arrangement of the back of the mouth/pharynx area such that at least one electrode is positioned proximate a specific muscle or muscle layer. In some embodiments, the probe may comprise a flexible printed circuit board (FPCB), and the plurality of electrodes may be arranged in an array.

In some embodiments, the size and shape of the probe can be configured for placement of the at least one electrode adjacent at least one of the soft palate, pharyngeal wall and tongue, and the thermal sensor can be configured to output temperature signals corresponding to the temperature of at least one of the soft palate, pharyngeal wall and tongue. For example, the size and shape of the probe can be configured such that the at least one sensor contacts the Levator Palatini, Tensor Palatine, Palatopharyngeus, Palatoglossus, Muscularis Mucosae, Musculus Uvulae and/or the like. In some embodiments, the size and shape of the probe may be configured to effect placement of the at least one sensor proximate at least one of the soft palate, pharyngeal wall, and tongue, and the computer instructions may be additionally configured to cause the processor to determine at least one of the quality and condition of at least one of the muscle, nerve and tissue dynamics of the soft palate, pharyngeal wall, and tongue.

In some embodiments of the present disclosure, the at least one sensor of the system may comprise an array of sensors, wherein the size and shape of the probe are configured to effect placement of each sensor proximate one or more muscle layers of at least one of the soft palate, pharyngeal, and tongue, and the computer instructions are additionally configured to cause the processor to determine whether spontaneous EMG activity or abnormal MUP's comprises opposite side synchronization and symmetry of the EMG activity of at least the palate, and comparing the EMG activity with that of EMG activity of a non-apnea patient.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1:
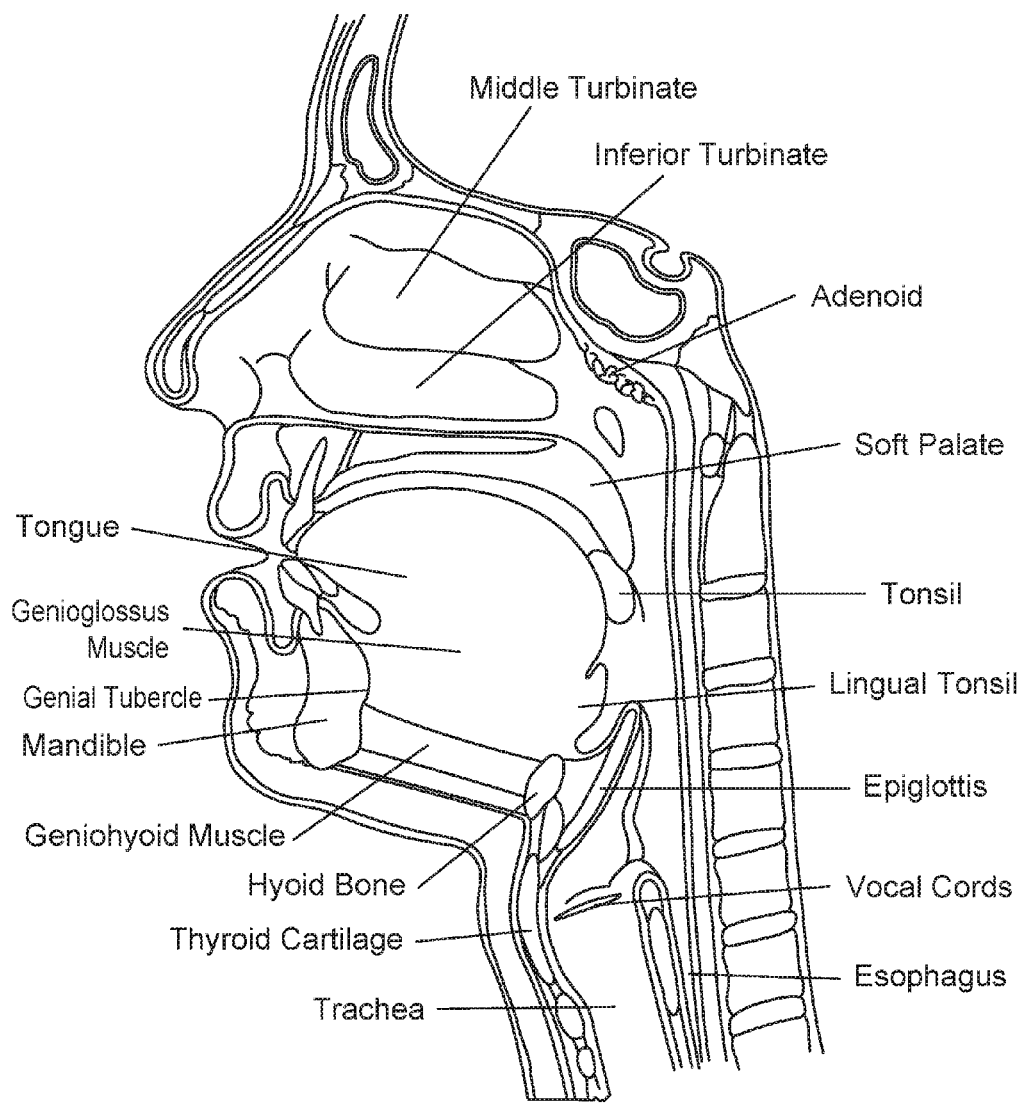
FIG. 1 shows an example embodiment of anatomic imaging illustrating sites of potential airway obstruction for some sleep disorders, examples of which include nose, palate and hypopharynx.

In some embodiments of the present disclosure, an electromyography (EMG) probe (and in some embodiments, an EMG/thermal probe), is provided which may be used as a diagnostic tool for at least one of assessing, analyzing, diagnosing, and recording electrical activity occurring in the tissues/organs of a patient's body. In such embodiments, the quality and/or status of the neuromuscular and tissue dynamics may be determined, which can aid in the diagnosis and/or treatment of conditions associated with said tissues and/or organs. To enhance the understanding of some of the embodiments taught by the present disclosure, a basic primer of the electrical properties of nerve and muscle is provided, as well as basic electrophysiological characteristics of neuromuscular pathology and how those are assessed electrophysiologically.

Electrophysiology Primer

Excitability of tissues, whether nerves or muscles, is reflected in the magnitude of the transmembrane potential in a steady state. If a threshold is reached during stimulation, an action potential is generated that propagates across the membrane. Such action potentials convey information about the nervous system, as they originate in the cell body or axon terminal and propagate along nerve fibers. EMG can be used to analyze these electrical properties in various skeletal muscles at rest and during voluntary contraction.

Clinically, these extracellular action potentials may be recorded during electro-diagnostic procedures through surface or needle electrodes. Interstitial fluid and connective tissue act as volume conductors surrounding the generator sources. A volume conductor, which can be referred to as a source, is a container in which electrical events are transmitted over distance. Such sources are represented as dipoles—made up of positive and negative regions. Dipoles give rise to voltage differences between the active recording electrode in a high current density area and a distant reference electrode.

The position of the recording electrode relative to a generator source determines the direction of the recorded waveform potentials (i.e., negative versus positive). In a muscle cell, an electrical potential exists across the cell membrane, as the interior of the cell is slightly negatively charged with respect to outside the cell. Moreover, the cell's sodium-potassium pump functions to maintain a small potential difference across the cell. To that end, depolarization, to a critical/threshold level, opens the sodium channels, allowing permeability leading to nerve excitation. This all-or-none response of nerves and muscles is intrinsic—the action potential occurs as long as depolarization reaches a critical level.

A motor unit comprises a group of muscle fibers innervated by a single anterior horn cell. The shape of a motor unit potential (MUP) may reflect many physiologic factors including resistance and capacitance of intervening tissue and intramuscular temperature. For example, hypothermia can result in a decrease in MUP amplitude, increased MUP duration, and increased number of MUP polyphasic potentials.

Recruitment describes the pattern in which healthy muscle is excited with only one or two motor units before recruiting additional units. These motor units typically discharge at 5-7 impulses per second, semi-rhythmically, with slowly increasing, then decreasing, interspike intervals. Interference pattern describes the pattern of increasing motor units firing rapidly with greater muscle contraction.

At rest, a pair of electrodes placed on the surface of a muscle registers no potential difference between them. Thus, EMG recording of a normal muscle at rest is silent. During muscle activation, as the propagating action potential reaches the near electrode (G1), then G1 becomes negative relative to the distant electrode G2 resulting in an upward deflection of the tracing, followed by neutral deflection (or baseline), followed by downward deflection, and finally neutral deflection (or baseline).

Using surface EMG, according to some embodiments, data analyses of the frequency and time domain can give rise to an average estimate from many motor units at different contraction levels.

Electrodes

In some embodiments, bipolar electrodes are used, in that a reference electrode is arranged at a distance from the active electrode. Such electrodes comprise surface electrodes which are placed over muscle and record summated activities from a plurality of muscle motor units, as compared to needle electrodes inserted into muscle which can record individual MUPs during mild muscle contraction.

Recognizing Artifacts

In some embodiments, biologic EMG activity will need to be differentiated from artifacts. This is due to the challenging palatal environment. Any voltage not attributable to the biologic potential sought, in some embodiments, represents an artifact (e.g., 60 Hz electromagnetic AC circuit noise, cardiac pacemaker, EKG artifact, movement artifacts, etc.). Artifacts may be detected via EMG through at least one of visual and auditory representations.

To address artifact issues, electrical signals detected from a patient may be filtered and/or amplified such that spontaneous activity can be recognized Filtering may be used to optimize the signal to noise ratio (SNR) of signals. For example, a high frequency (low pass) filter may be used to reduce the amplitude of high frequency components (e.g., if set too low). A low frequency (high pass) filter can distort slowly changing potential, if set too high. Accordingly, in some embodiments, bandpass frequencies may be set with low frequency filters at 10 Hz (for example) and high frequency filters at 1000 Hz (for example). In addition, in some embodiments, electrode locations, shape, and/or distance between electrodes may be optimized for each patient to increase the signal-to-noise ratio (SNR).

With respect to amplification, differential amplifiers may be used to amplify the voltage difference between, for example, the input terminals (two) connected to the recording electrode, as opposed to between input terminals and the ground. This arrangement can be used to address artifacts produced as a result of AC power (for example), as well as distant muscle action potentials common to both. Amplifiers may comprise several stages to increase the gain of the signal to noise (SNR) ratio by amplification of the signal near the source, prior to the emergence of noise that develops in the circuits (for example). A preamplifier may also be used which may include high input impedance, low noise level, and a large dynamic range (for example). Given the large range in amplitude of biologic EMG activity, threshold settings to capture the majority of data, and limiting or eliminating artifact data may be realized in some embodiments. Sensitivity for electrodes may be set at 50 uV/division and sweep speeds may be set at 10 ms/division. In some embodiments, threshold capture may be established at 100 uV.

For EMG, a multistage differential amplifier may be used to achieve high net gain (although differential amplifiers also have high input impedance). Because voltage drop is large when impedance is high and voltage drop equates to useful work performed, amplification, in some embodiments, is best when the voltage drop occurs at the amplifier rather than at the patient electrode connections. Maintaining low impedance connections to the patient can minimizes interference and may also maximize amplification.

Likewise, common mode voltages too large to be perfectly balanced typically overload an amplifier. In addition, the impedance in an AC circuit determines current flow and impedances for recording muscle action potentials are greatest at the electrode tip and input terminals of the amplifier. Accordingly, an amplifier with a high input impedance improves the common-mode-rejection-ratio (CMRR) because the higher the input impedance, the smaller the effect of electrical asymmetry of the recording electrodes.

Since unequal impedances of two recording electrodes may produce unequal effects from any common mode signal (resulting in impairing the effectiveness of the differential amplifier, decreasing the CMR, and increasing the interference), impedances may be assessed in each patient for each electrode in each position to achieve less than 5 kOhms (for example), according to some embodiments.

In some embodiments, to minimize electromagnetic interference, other measures may be used including reducing and balancing contact impedances of the electrodes may be used, as well as using short, well-shielded electrode cables. This includes avoiding unshielded power cords to other devices in the vicinity.

In some embodiments, an analog to digital convertor (ADC) may be used which changes the analog signals from sensors (e.g., electrodes) into a discrete digital approximation. The accuracy of the digital replication of an analog signal depends on how often the signal is sampled (sampling frequency) and on the number of discrete digital steps available to quantitate the amplitude (vertical resolution). A high sampling frequency and a large number of steps will produce a more accurate digital replica.

Probe Applications

Some embodiments of the present disclosure may be used to at least diagnose and treat various conditions and to correct damaged soft tissues, muscles, nerves and vascularization associated with the conditions. This may be accomplished, in some embodiments, by analysis of surface EMG and/or thermal activity of the tissues, muscles, etc. For example, sleep apnea/OSA may be diagnosed by analysis of EMG and/or thermal activities of the soft palate and pharynx regions. As another example, probing muscle function in the middle ear such as the tensor tympani may allow for the diagnosis of, for example, tinnitus. Other conditions that may be diagnosed via the tympanic application of surface EMG probes include vertigo (including vestibular neuronitis, vestibular migraine, Meniere's disease, benign paroxysmal positional vertigo (BPPV)), hearing loss, sudden sensorineural hearing loss, calcium deposition in the inner ear, ototoxicity, vestibulotoxicity, etc. In some instances, probes may be used during surgeries. For example, probes may be employed for intraoperative monitoring of inner ear function during acoustic neuroma surgery.

In some embodiments, trans-conjunctival EMG probes can be used to at least diagnose and treat neurological disorders. Examples of such neurological disorders include Battaglia Neri syndrome, dermatomyositis, diabetic neuropathy, encephalitis, meningitis, multiple sclerosis, myasthenia gravis, Parkinson's disease, subacute sclerosing panencephalitis, and/or the like. The probes may also be used to diagnose and treat eye conditions. Examples include esotropia (e.g., accommodative esotropia, etc.), exotropia, Brown syndrome, convergence insufficiency, dissociated vertical deviation, Duane syndrome, oculomotor apraxia, and/or the like. In some embodiments, the conditions to be diagnosed may not be specific eye conditions, but may be materially related, such as abnormal head position, conjugate gaze palsies, internuclear ophthalmoplegia, microvascular cranial nerve palsy, monocular elevation deficiency (i.e., double elevator palsy), palsies of cranial nerves, progressive supranuclear palsy, pseudostrabismus, and/or the like.

In some embodiments, various muscle groups can be accessed via major blood vessels by, for example, placing a probe with transvascular EMG through blood vessels and onto a muscle group in a location adjacent to the blood vessel. For example, heart muscle activities such as, but not limited to, myocardial muscle functions may be evaluated and assessed using trans-endovascular probes that sense, and in some embodiments further analyze EMG activities of associated tissues. Examples of diseases, conditions, etc., that can be diagnosed and/or treated include transient conditions of chronic autonomic dysfunction related to cerebrovascular disease, myocardial infarction, ischemic muscle tissue, valvular disease and muscle function, left ventricular dysfunction arrhythmia, degenerative brain disorders present with myocardial disease, degenerative neurologic conditions, cardiomyopathy, neuromuscular disorders, mitochondrial myopathies, dystrophies, cardiac conduction defects, and/or the like.

Some embodiments of the present disclosure may be used to probe gastrointestinal and/or related tissues/organs. Such probes may allow the diagnosis and treatment of conditions such as dysphagia which may involve any of pharyngeal muscles, cricopharyngeus, esophageal muscles, lower esophageal sphincter, pancreatic sphincter, bile duct sphincter, etc. In some embodiments, some neurological diseases may be associated with bowel disorders, and such diseases/conditions may be diagnosed and treated with the aid of gastrointestinal surface EMG probes. Examples of such conditions/diseases include Ogilvie syndrome, gastrointestinal neoplasm, gallstone ileus, intestinal adhesions causing obstruction, volvulus, intussusception, amyotrophic Lateral Sclerosis, Brown-Sequard syndrome, Central Cord syndrome, Multiple sclerosis, Parkinson disease, spina bifida, Spinal Cord Injury, lesions and aging, diabetes mellitus, and/or the like.

Another example embodiment of the uses of the surface EMG probe discussed in the disclosure herein can be in the field of urological diagnosis and treatment. In some embodiments, the probe may be used to address vascular issues, examples of which include renovascular hypertension, and problems associated with external and/or internal vessels of the bladder. Such problems may be post-radiation changes, over-active bladder, interstitial cystitis, internal and external urethral sphincter related issues (e.g., post radiation changes, bladder neck contraction, etc.), spermatic cord problems, cremasteric muscle spasms, varicocele, and/or the like. In some embodiments, the probe may also allow for the diagnosis and treatment of conditions/diseases associated with the renal pelvis and the ureter, which involve mucosal membranes. For example, conditions such as congenital malformations may be detected prenatally in utero using the probe. As another example, the probe may aid in the diagnosis of ureteropelvic junction (UPJ) obstruction, which may be a scar, the so-called crossing vessel, overactive muscles, etc. With reference to the ureter, in some embodiments, the probe may be sized and made flexible so as to facilitate that the proper diagnosis of any problems with the ureter, examples of which include mega ureter, ureterectasis, hydronephrosis, etc. In addition, the probe maybe used to diagnose Ureterovesical Junction (UVJ) related complications, such as but not limited to vesicoureteral reflux (VUR).

Other example embodiments of urological applications of the surface EMG probe comprise diagnoses and treatments of the bladder and the prostate. Examples of conditions and/or diseases of the bladder include overactive bladder (OAB), neurogenic bladder (e.g., with or without spinal cord injury), chronic obstructive uropathy, complications due to spinal cord injury, detrusor-sphincter dyssynergia, urethral stricture (e.g., one can check for muscle/scar function or just scar), interstitial cystitis, and/or the like. Examples of urological applications related to the prostate include the diagnosis and treatment of prostatodynia, determination between cryptorchid and retractile testis (e.g., due to overactive cremasteric muscle), diagnosis of fertility affecting issues such as obstruction of ejaculatory duct and/or the opening thereof (verumontanum), epididymal obstruction, Vas Deferens immotility, and/or the like.

With reference to FIG. 1, in some embodiments, anatomic imaging illustrating sites of potential airway obstruction for some sleep disorders, examples of which include nose, palate and hypopharynx, is shown. Some embodiments of the present disclosure may be used to at least diagnose and treat sleep apnea/OSA to correct damaged soft tissues, muscles, nerves and vascularization in such areas. This may be accomplished, in some embodiments, by analysis of EMG and/or thermal activity of the soft palate and pharynx regions.

In some embodiments, detection of spontaneous activity in a muscle at rest or MUP's that are large, wide, polyphasic or poorly recruited is considered abnormal. Similar to the heart, the muscles of the mouth/throat/palate generate an electrochemical impulse that spreads out so as to cause the cells to contract and relax in a timely order synchronized with the breathing. This sequence is initiated by a depolarization of the muscle and tissue cells of the palate. Because this action is electrical in nature and the body is conductive with its fluid content, this electrochemical action can be measured at the surface of the body. Thus, using the systems, methods and devices according to one or more of the embodiments taught by the present disclosure, normal/abnormal pharyngeal EMG can be assessed in some embodiments. In addition, the EMG findings and left/right side synchronization and symmetry of the dynamic operation of the palate (for example) can be analyzed and recorded. Accordingly, in some embodiments, such EMG findings can be compared to data for non-apnea patients for determination of OSA, for example.

In some embodiments, for measuring EMG in the palate/throat, one or more sensors, e.g., electrodes, may be provided on a probe, which are configured to determine EMG activity in the throat area. For normal pharyngeal EMG, during sleep, EMG activity could be silent. If spontaneous EMG activity occurs or abnormal MUP's are present in the EMG tracing, a neuromuscular pathology may exist, which may be indicative of OSA. Spontaneous activity includes fibrillation potentials, positive sharp waves, complex repetitive discharges, fasciculation potentials, myokymic discharges and/or the like. The presence of any true biologic spontaneous activity may be noted as abnormal. Parameters/characteristics of abnormal MUP's includes MUP's that are large, wide, polyphasic or exhibit a poor recruitment pattern.

Similarly, the contraction and relaxation of muscles in other parts of the body located in close proximity to membranous tissue generate electrical activity that may be detected and assessed according to some of the embodiments of the present disclosure. For example, the tympanic muscle in the middle ear connected to the malleus may contract in response to loud noises, and such movements generate electrical activities that can be detected by a surface EMG probe in communication with the tympanic membrane. In some embodiments, the probe or sensor may be placed topically on the surface of the tympanic membrane via rigid telescope. In some embodiments, the sensor may also be configured to probe the inner ear. For example, the sensor may be configured to be placed topically on inner ear membranes such as the round window membrane, the oval window membrane, etc., that separate the inner ear from the middle ear, and sense EMG activities in proximity to such membranes. Such sensors can be used in situ during surgeries, for example, for intraoperative monitoring of inner ear function during acoustic neuroma surgeries.

In some embodiments, the sensor may also be configured to be placed topically in targeted areas of the eye to measure EMG activity of the extraocular muscles through the conjunctival membrane. These muscles could include medial rectus, lateral rectus, superior rectus and inferior rectus.

In some embodiments, the sensor may also be configured to pass through an endoscope or laparoscope to be placed topically on membranes in targeted areas of the gastrointestinal (GI) tract to measure EMG activity of muscles associated with GI function such as pharyngeal muscles, cricopharyngeus, esophageal muscles, lower esophageal sphincter, pancreatic sphincter and bile duct sphincter.

In some embodiments, the sensor may also be configured to pass through a catheter tube to be placed topically on membranes in targeted areas of the heart to measure EMG activity of the myocardium.

In some embodiments, the sensor may also be configured to pass through an endoscope to be placed topically on membranes in targeted urologic areas of the body to measure EMG activity of muscles associated with urologic functions such as detrusor muscle, urethral sphincter, bladder, and/or the like.

In some embodiments, the sensor may register from a muscle an EMG activity that deviates from a benchmark activity (e.g., expected results) indicating the occurrence of some type of abnormality with the muscle. For example, the benchmark activity level may be silence (i.e., no activity), and as such any registered spontaneous EMG activity may indicate diseases/conditions such as the ones discussed above with reference to probe applications. In some embodiments, the benchmark activity level may establish a "normal" EMG activity, and deviations from the benchmark beyond some tolerance threshold, may be viewed as "abnormal". For example, the benchmark activity may indicate a specified EMG intensity level, frequency of EMG activity, duration of EMG activity, etc., along with tolerance ranges, and detected/recorded EMG activity that falls within the tolerance ranges of the benchmark activity may indicate normal muscle behavior while activities falling beyond the tolerance ranges may indicate abnormal behavior. Examples of EMG activities comprise neuropathic changes such as decreased numbers of motor unit potentials (MUPs), and higher firing rate of MUPs. As such, a benchmark level may be a specified number and/or firing rate of MUPs, and the tolerance ranges may be deviations from the specified number and/or firing rate, respectively. In the case of EMG activities related to sleep, neuropathic changes such as polyphasic MUPs with long duration, and/or high amplitude may indicate affliction with OSA if, for example, the registered duration, frequency, amplitude, etc., of the MUPs fall outside of the tolerance ranges of MUP benchmark activity. Other examples of EMG activities comprise myopathic changes such as but not limited to decreased recruitment of MUPs and spontaneous activities, examples of which include fibrillations, positive sharp waves, complex repetitive discharges, myotonia, and/or the like. In some embodiments, there may be more than one threshold levels, and spontaneous EMG activity may be classified according to the multi-threshold grading system. For example, the multi-threshold grading may comprise four levels, indicating rare, occasional, frequent and abundant levels of spontaneous EMG activities. In some embodiments, these levels, i.e., grading scales may be reader dependent measures. For example, each EMG reader may visually quantify the amount of activity they see in the EMG tracing on a screen and grade it based on this scale. As an example, rare may denote MUP that fill a fraction of the screen (e.g., about or less than a quarter of it), and abundant may correspond to MUPs that fill a large portion (e.g., about or more than three quarter) of the screen. In some embodiments, the gradings may correspond to any activity levels between a single MUP on the screen to MUPs filling the screen, with rare, occasional, frequent and abundant corresponding to increasing amount of MUP. In some embodiments, the grading may comprise any number of scales (e.g., from 0 to 10 with 0 indicating few or no EMG activity level and 10 indicating a substantially large or maximum amount, etc.).

Figure 2:
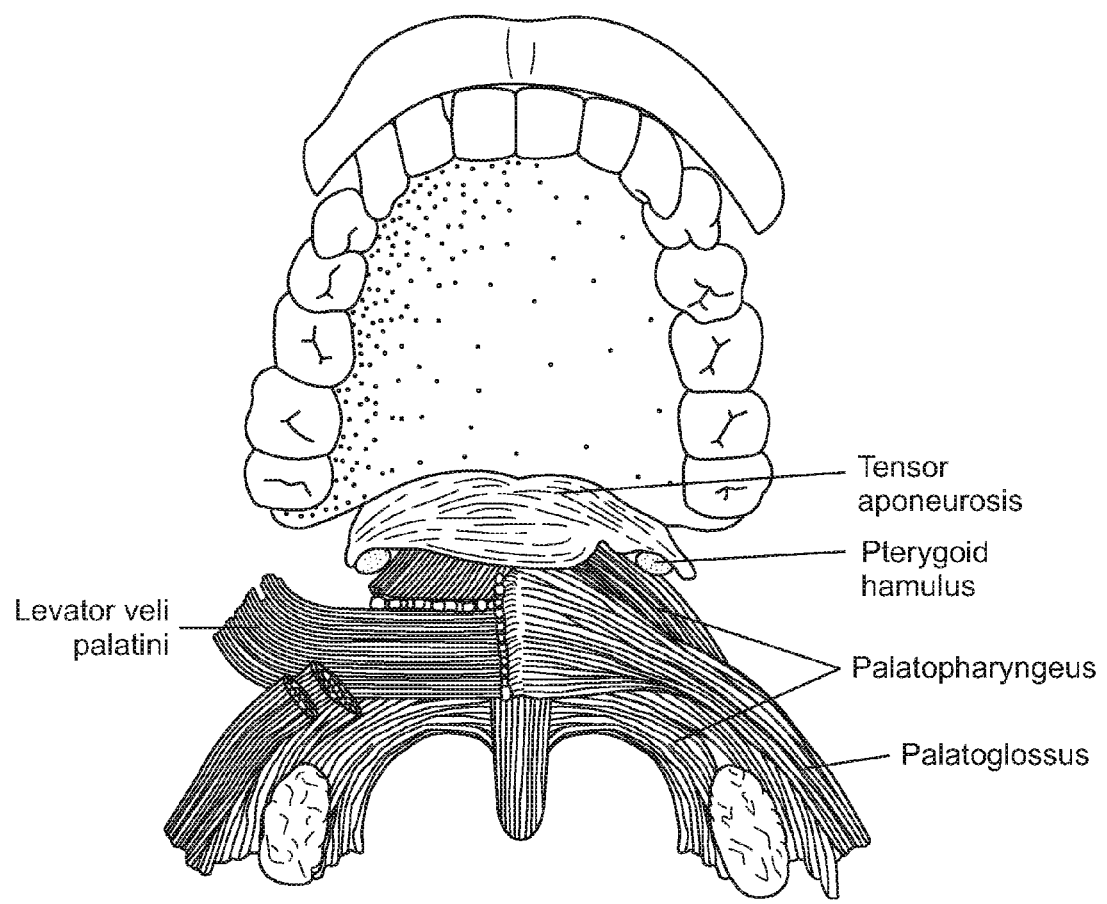
FIG. 2 illustrates example muscle structures of the back of the mouth/pharynx, to which sensors/electrodes can be arranged on a probe for capturing muscle data thereof.

With reference to FIG. 2, in some embodiments, the muscle structures of the back of the mouth/pharynx, to which sensors/electrodes can be arranged on a probe for capturing muscle data thereof are illustrated. In some embodiments, electrodes may be affixed to a surface of a mouth/throat probe and arranged such that when the probe is positioned in the back of the mouth/throat, the electrodes align to the muscle layers of at least one of the soft palate, lateral pharyngeal wall, and tongue (the probe shape may be configured to limit contact points to limit, for example, a gag response). EMG and thermal data corresponding to signals generated from the electrodes of the underlying muscle may be collected and identified with specific individual muscles of at least one of the palate, lateral pharyngeal walls (including, for example, the Levator Palatini, Tensor Palatine, Palatopharyngeus, Palatoglossus, Muscularis Mucosae and Musculus Uvulae), and/or tongue. In some embodiments, the collected EMG and thermal data may be analyzed to assess and diagnose the quality and condition of the muscle, nerve and tissue dynamics, and may also be used to diagnose OSA.

Figure 3A:
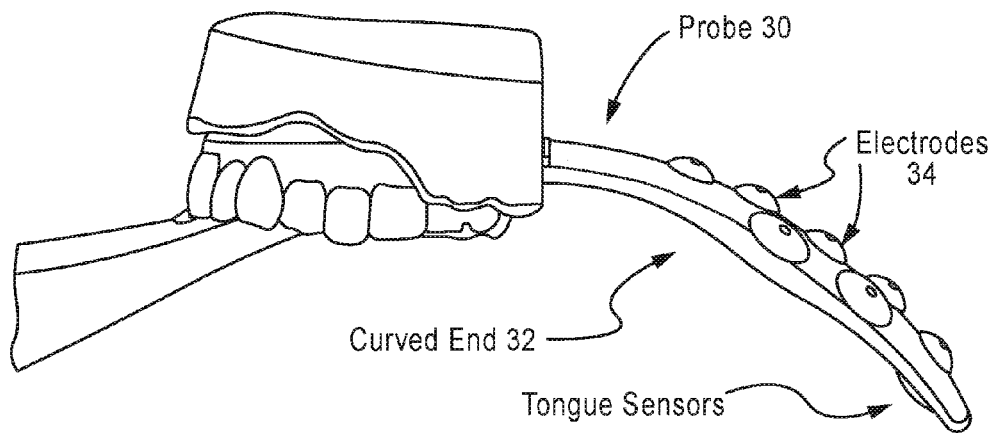
FIGS. 3A-F show example embodiment of a probe device configured for placement within a mouth.
Figure 3B:
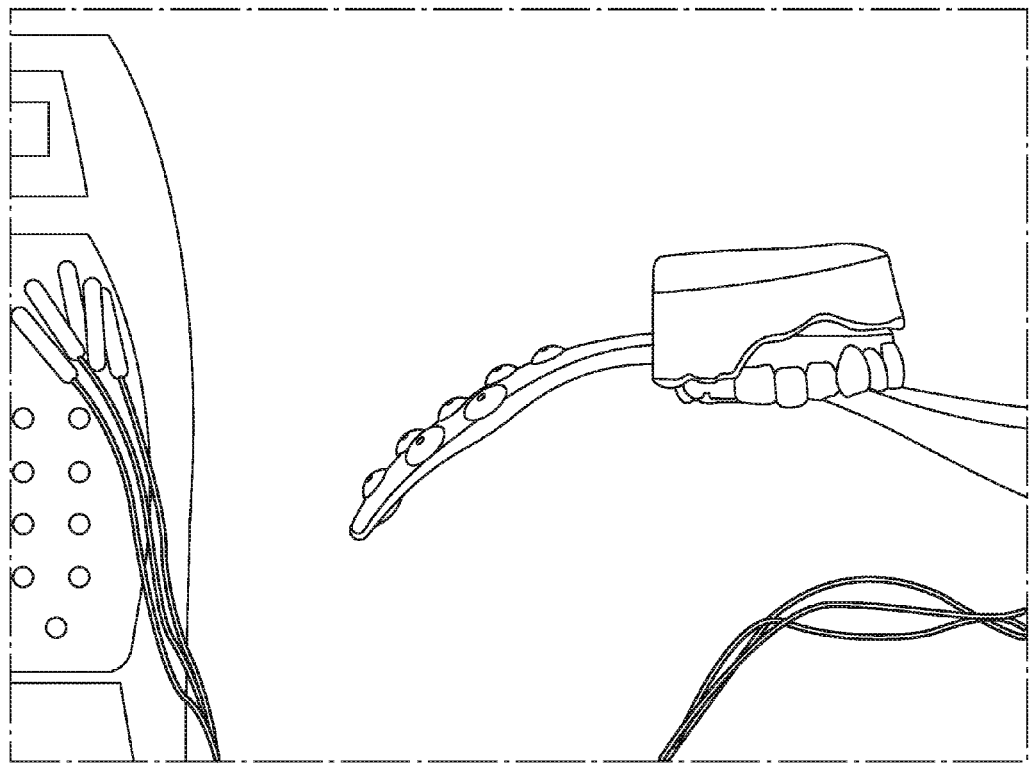
Figure 3C:
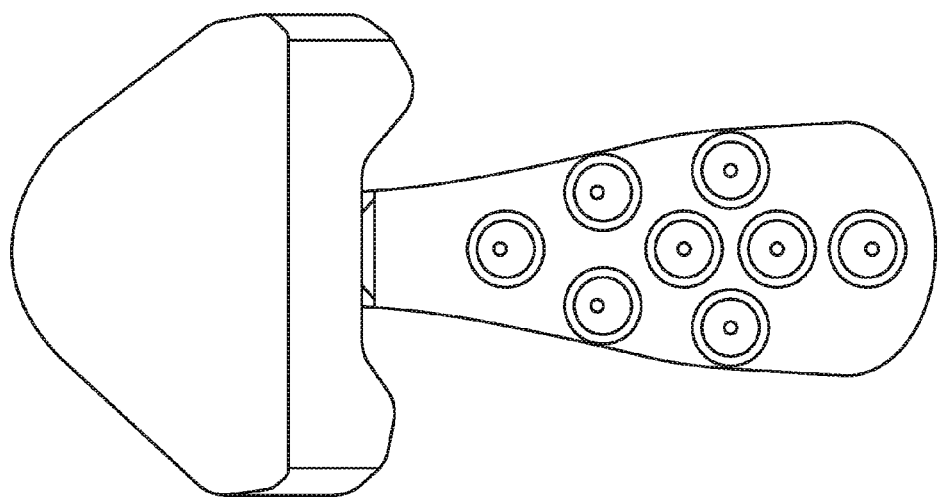
Figure 3D:
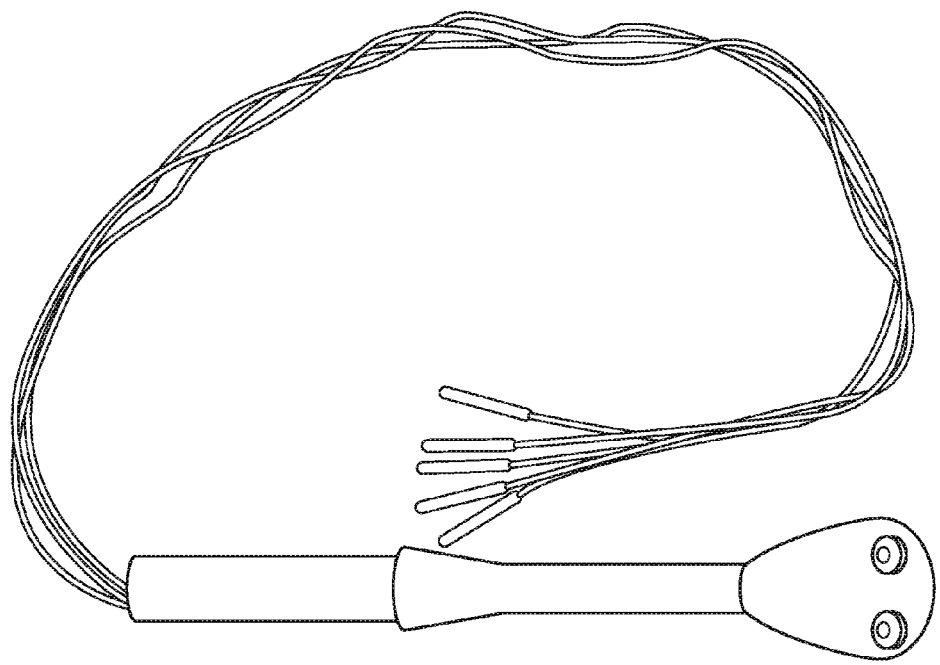
Figure 3E:
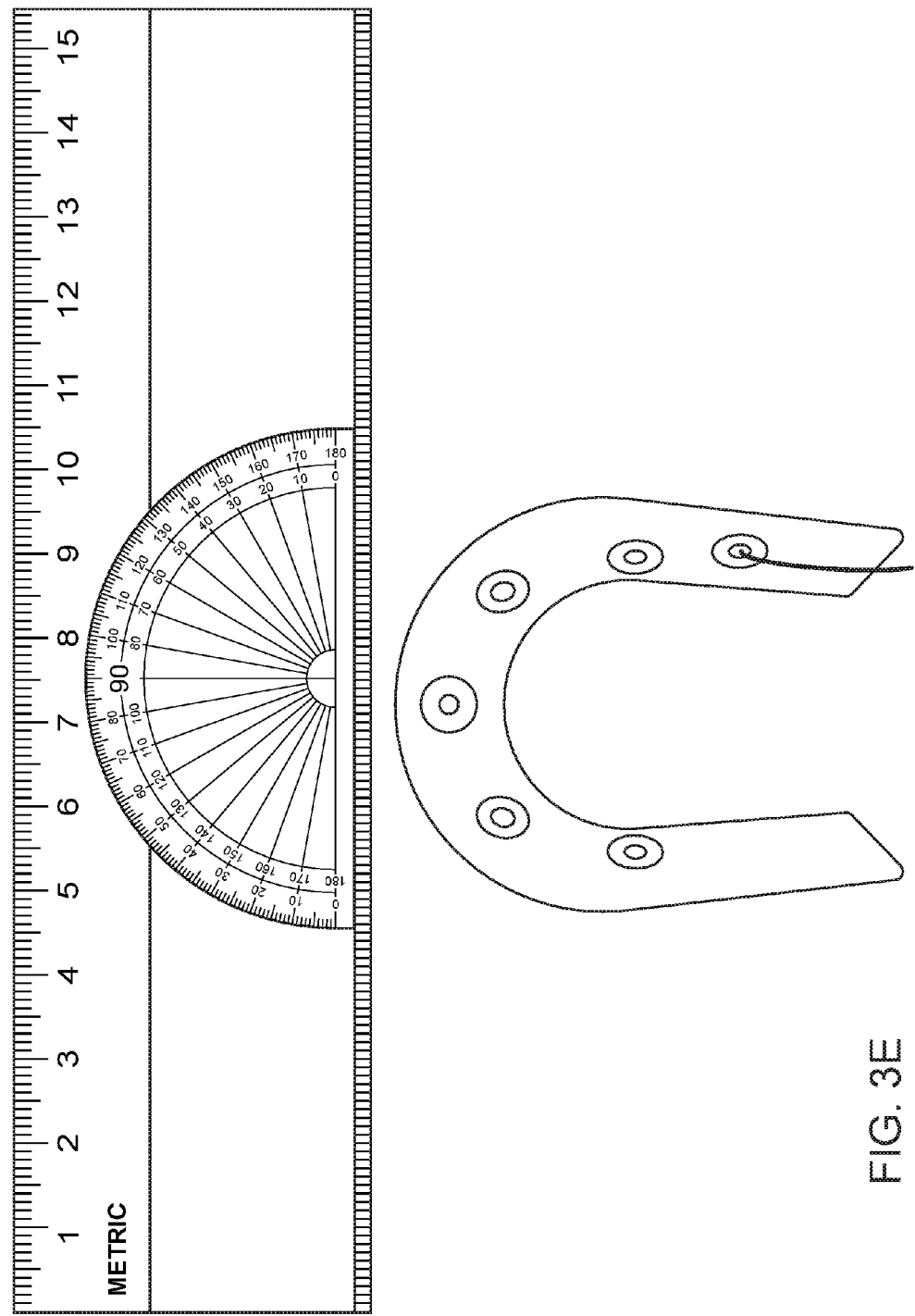
Figure 3F:
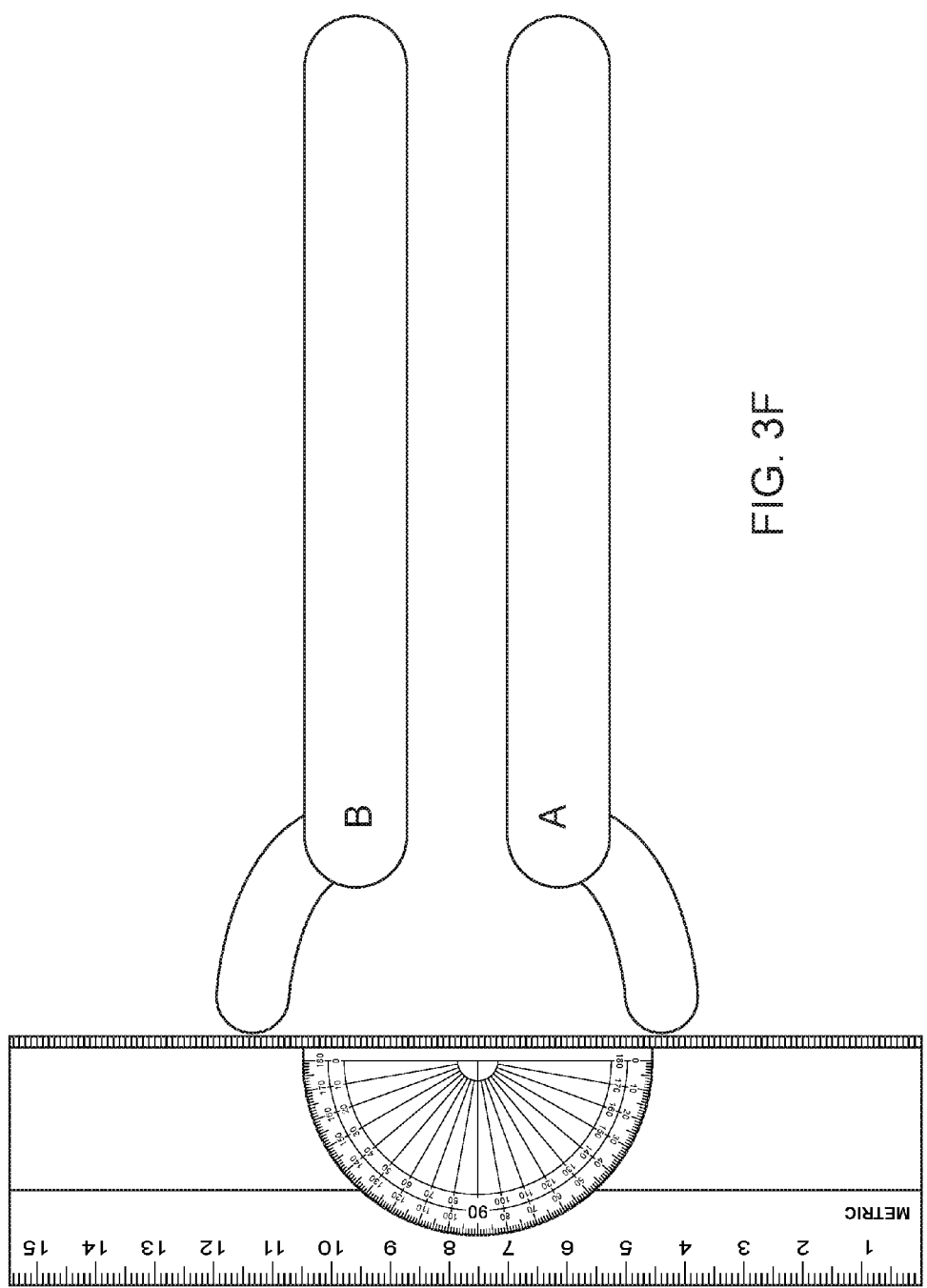

With reference to FIGS. 3A-3F, example embodiments of a probe device configured for placement within a mouth are shown. In some embodiments, probes can be configured with the size and shape to effect their placement at a location where the sensor can detect EMG activity of a muscle. For example, a probe can be sized and shaped so as to allow its placement on the round window membrane when measuring EMG activity in the middle ear. FIGS. 3A-3F show an example probe including a curved end, which may be configured with a size and/or shape for being easily received and positioned in the mouth/throat of a patient. The probe includes one or more sensors, which may be electrodes. In some embodiments, such sensors/electrodes may comprise a heat sensor, or the sensor may be a combination of an electrode and a heat sensor. Accordingly, FIG. 3A shows a side view of the probe according to some embodiments, having a shape conforming to the structure of a patient's mouth. For example, the end portion of the probe is placed adjacent at least one of the soft palate, pharyngeal wall, and tongue of a patient. FIG. 3B shows another side view of a probe according to some embodiments, where the probe device is connected to a measuring device to process signals (e.g., information) generated from sensors (e.g., electrodes, and/or thermal) provided with the probe. FIG. 3C is a top view of a probe according to some embodiments, illustrating an end portion having a plurality of spherical electrodes. FIG. 3D is another top view of a probe according to some embodiments. In some embodiments, tongue sensors/electrodes (which may also include thermal sensors) may be included for capturing spontaneous muscle data (e.g., FIGS. 3A and 3D). FIGS. 3E-3F show an example probe in comparison to a measuring scale to illustrate the size and shape of the probe.

In some embodiments, such probes may be used in a system for aiding in the diagnosis of OSA. For example, they may comprise an elongated member configured with a size and shape for insertion into the mouth of a patient, an end configured for placement adjacent at least one of the soft palate, pharyngeal wall and tongue of the patient after insertion of the probe into the mouth of the patient, and at least one sensor configured to sense at least EMG activity of muscle layers of at least one of the soft palate, pharyngeal wall, and tongue, and output sensor signals corresponding thereto.

In some embodiments, a system for aiding in the diagnosis of Obstructive Sleep Apnea (OSA) is provided which may comprise a probe having at least one sensor (e.g., see above), and a processor having computer instructions operational thereon configured for causing the processor to monitor the sensor signals for EMG activity, and determine whether the sensor signals of EMG activity correspond to spontaneous EMG activity or abnormal MUP's.

In some embodiments, a method for aiding in the diagnosis of OSA is provided and includes providing a probe having at least one sensor (e.g., see above), monitoring the sensor signals for EMG activity, and determining whether the sensor signals of EMG activity correspond to spontaneous EMG activity or abnormal MUP's. In some embodiments, spontaneous EMG activity of muscles or abnormal MUP's of at least one of the soft palate, pharyngeal wall and tongue, may be an indication of OSA. Such method(s) may be performed via software operable on a computing device (according to some embodiments).

In some embodiments of the present disclosure, determining spontaneous activity comprises determining whether the sensor signals comprise at least one of fibrillation potential positive sharp waves, complex repetitive discharge, fasciculation potentials, and myokymic discharges. In some embodiments of the present disclosure, determining abnormal MUP's comprises measuring the MUP's to determine MUP parameters such as size, shape, complexity, amplitude, phase, duration, area frequency, and/or the like. In some embodiments, the above-noted method may further comprise differentiating EMG activity of the muscle layers of at least one of the soft palate, pharyngeal wall and tongue from EMG artifacts, where upon a determination of spontaneous EMG activity or abnormal MUP's, the method further comprises grading the spontaneous EMG activity, by, for example, determining one or more periods of occurrence of the spontaneous EMG activity. In some embodiments, the periods comprise at least one of rare, occasional, frequent and abundant positive sharp waves, complex repetitive discharge, fasciculation potentials, and myokymic discharges. In some embodiments, the above-noted method may further comprise differentiating EMG activity of the muscle layers of at least one of the soft palate, pharyngeal wall and tongue from EMG artifacts, where upon a determination of spontaneous EMG activity or abnormal MUP's, the method further comprises grading the spontaneous EMG activity, by, for example, determining one or more periods of occurrence of the spontaneous EMG activity, or measuring the size, shape, amplitude, phase, duration, area, complexity, frequency, etc., of the MUP's. In some embodiments, the periods comprise at least one of rare, occasional, frequent and abundant.

In some embodiments of the present disclosure, one or more of the following features may be included for any method, system, probe, device or otherwise taught by the present disclosure:
- the at least one sensor comprises an electrode;
- the at least one sensor comprises a plurality of sensors, where each sensor comprises an electrode;
- the at least one sensor comprises at least one electrode, and at least one of the electrode includes a thermal sensor;
- the at least one sensor comprises an electrode which is spherical;
- sensors/electrodes being provided (in embodiments providing a plurality thereof), are spaced apart from an adjacent electrode by about 5 mm (for example);
- the at least one sensor comprises a thermal sensor configured to output temperature signals of the temperature of at least one of the soft palate, pharyngeal wall and tongue;
- the probe is configured with a size and shape such that the at least one sensor contacts at least one of the Levator Palatini, Tensor Palatine, Palatopharyngeus, Palatoglossus, Muscularis Mucosae and Musculus Uvulae.
- determining the quality and condition of at least one of the muscle, nerve and tissue dynamics of at least one of the soft palate, pharyngeal wall, and tongue;
- the probe further comprises a flexible printed circuit board (FPCB), where the at least one sensor is provided;
- the at least one sensor comprises a plurality of sensors and wherein the sensors may comprise electrodes arranged in an array;
- the at least one sensor comprises an array of sensors each configured to sense at least EMG activity of muscle layers of at least one of the soft palate and pharyngeal;
- determining whether the sensor signals of EMG activity corresponds to spontaneous EMG activity or abnormal MUP's includes determining opposite side synchronization and symmetry of the EMG activity of at least the palate;
- comparing the EMG activity/data of a patient with the EMG activity of a non-apnea patient to determine whether the patient's EMG activity is indicative of OSA; and
- at least one of filtering and amplifying signals generated by sensors.

Figure 4:
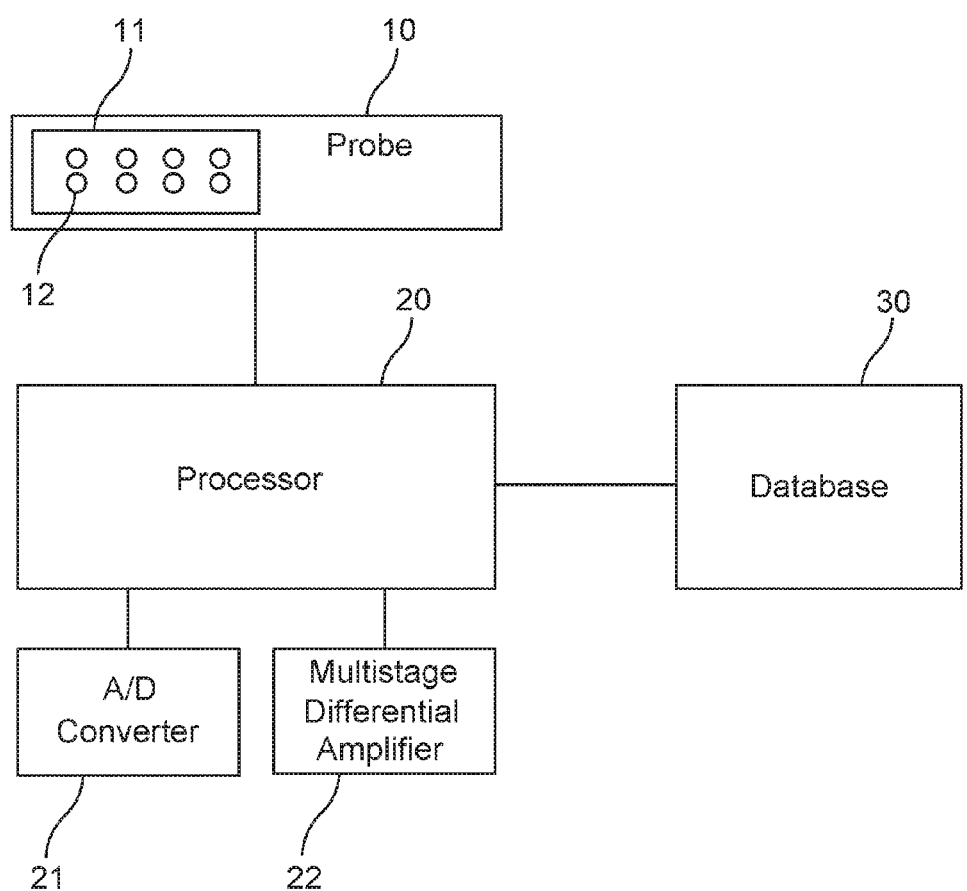
FIG. 4 shows an example block diagram depicting some or all components of a probe device disclosed herein.

With reference to FIG. 4, in some embodiments, a block diagram of a probe device 10 designed for probe applications discussed above is shown. In some embodiments, probe electrodes 12 may be configured on a printed circuit board (PCB) arranged in an array of individual electrode contacts, which may be positioned on one end of the probe that may be curved. In some embodiments, the distance between the sensors/electrodes 12 can vary depending on the selection of the overall probe size. In some embodiments, the end of the probe 10 may be configured in a small, medium and large size, each subsequent size configured with a slightly larger curved surface, and therefore, a greater distance between sensors (for example). Such size configurations may accommodate differences in particular patient anatomies, differences in gender specific anatomies, as well as allow for the use of the probe/sensor(s) in children.

For example, in some embodiments, tongue based sensors/electrodes (which may also include thermal sensors) are provided (either in addition to or as a stand-alone device) to capture tongue based muscle data. For instance, a probe device configured for insertion into a mouth for sensing EMG activity may include a flexible PCB to which a plurality of surface spherical electrodes of about 5 mm width (for example), with 5 mm (for example) inter-electrode distance, reside. In some embodiments, the width of one or more electrodes is configured to correspond to the anatomical arrangement of muscles in the back of the mouth/throat/pharynx. For example, in some embodiments, each electrode is configured to capture EMG and/or thermal data of a specific muscle (e.g., side muscle) directly under the mucosa that is in contact with the sensor. For embodiments which include a 5 mm sensor size, such embodiments allow for variability in the position of the muscle under the mucosa. It is noted that each muscle is somewhat fan shaped, so that a broad (e.g., 5 mm) sensor/electrode may more accurately capture data than one that is pinpoint or smaller. In other embodiments, the sensor size may be between 1 mm and about 10 mm, in some embodiments, between 2 mm and 8 mm, and in some embodiments, between 3 mm and 6 mm, and in some embodiments between about 4 mm and about 5 mm. In some embodiments, a smooth and curved electrode surface probe may be used to accommodate the structure of the soft palate musculature and to reduce gag reflex.

As noted above, at least one, and in some embodiments, each electrode may include an additional sensor (e.g., thermal sensor) within the active and reference bipolar electrode. Accordingly, a probe may be connected to a processor 20 which may include computer instructions operating thereon to, for example, digitally process at least one of EMG/thermal signals (e.g., if analog sensor, converting such signals with an analog-digital converter 21, and optionally a multistage differential amplifier 22). Furthermore, the processor 20 may be connected to a database 30 which includes information on normal EMG activities of the muscle being sensed (e.g., comparison with EMG activities of non-apnea patients allows for determination of occurrence of apnea in the patient under monitoring). For example, instructions operating on the processor 20 can be provide which enables comparison of the EMG activity (for example) with that of EMG activity of a non-apnea patient.

Various implementations of the embodiments disclosed above (e.g., collection of EMG and/or thermal signals/data from a probe, filtering, amplification, and the like), in particular at least some of the processes discussed, may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions for a programmable processor, for example, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor and the like) for displaying information to the user and a keyboard and/or a pointing device (e.g., a mouse or a trackball) by which the user may provide input to the computer. For example, this program can be stored, executed and operated by the dispensing unit, remote control, PC, laptop, smart-phone, media player or personal data assistant ("PDA"). Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system according to some such embodiments described above may include clients and servers. A client and server are generally remote from each other and typically interact through a communication network. The relationship of client and server arises by virtue of computer programs running on the respective computers and having a client-server relationship to each other.

For example, such a system may include at least one device which is in communication (wired or wireless) with at least one controller/processor (as earlier noted). The processor communicates with at least one database, which may store data related to patients without OSA, as well as collected data from use with other patients. The processor may include computer instructions operating thereon for accomplishing any and all of the methods and processes disclosed in the present disclosure, including comparing collected EMG and/or thermal data of muscle activity in the throat stored in the database. Input/output means may also be included, and can be any such input/output means known in the art (e.g., display, memory, database, printer, keyboard, microphone, speaker, transceiver, and the like). Moreover, in some embodiments, the processor and at least the database can be contained in a personal computer or client computer which may operate and/or collect data from the detecting device. The processor also may communicate with other computers via a network (e.g., intranet, internet).

Similarly, a system according to some embodiments may be established as a server-client based system, in which the client computers are in communication with probe devices. The client computer(s) may be controlled by a server(s), each of which may include the database referred to above for storing information, and also be used to collect data (e.g., either or both may include the database). The client computers communicate with the server via a network (e.g., intranet, internet, VPN).

Any and all references to publications or other documents, including but not limited to, patents, patent applications, articles, webpages, books, etc., presented anywhere in the present application, are herein incorporated by reference in their entirety. In particular, the following references are incorporated by reference herein in their entirety:

1. Friberg D, Ansved T, Borg K, Carlsson-Nordlander B, Larsson H, Svanborg E.
Histological Indications of a progressive snorer's disease in an upper airway muscle. Ann J Respi Crit Care Med 1998; 157:586-93.
2. Woodson B T, Garancis J C, Toohill R J.
Histopathologic changes in snoring and obstructive sleep apnea syndrome. Laryngoscope 1991; 101:1318-22.
3. Namystowski G, Scierski W, Zembala-Nozynska E, Nozynska J, Misiolek M.
Histopathologic changes of the soft palate in snoring and obstructive sleep apnea syndrome patients.
Otolaryngol Pol 2005; 59(1):3-19.
4. Paulson F, Phillip P, Toskos M, Jungmann K, Muller A, Verse T, et al.
Upper airway epithelial structural changes in obstructive sleep-disoriented breathing.
Am J Respir Crit Care Med 2002; 166:501-9
5. Wasserman D, Badger D, Doyl L.
Industrial vibration and overview.
J Am Soc Safety Eng 1974; 19:38-43
6. Curry B D, Bain J L, Yanji G, Zhang L L, Yamaguchi M, Matloub H S, et al.
Vibration injury damages arterial endothelial cells.
Muscle Nerve 2002; 25:527-34.
7. Govindaraju S R, Curry B D, Bain J L, Riley D A.
Comparison of continuous vibration effects on rat-tail artery and nerve.
Muscle Nerve 2006; 34(2):197-204
8. Nelson B. Powell, Mihai Mihaescu, Goutham Myavarapu, Edward M. Weaver, Christian Guilleminault, Ephraim Gutmark.
Patterns in pharyngeal airflow associated with sleep-disorder breathing.
Sleep Medicine 12(2011):966-974
9. Terry Young, Mari Palta, Jerome Dempsey, James Skatrud, Steven Weber, Safwan Badr.
N Engl J Med 1993; 328:1230-5
10. Lee S A, Amis T C, Byth K, Larcos G, Kairaitis K, Robinson T D.
Heavy snoring as a cause of carotid artery atherosclerosis.
Sleep 2008; 31(9):1207-13
11. Rice T, Strollo P. Commentary on Jin-Cho et al.
Tissue vibration induces carotid artery endothelial dysfunction: a mechanism linking snoring and carotid atherosclerosis?
Sleep 2011; 34(6):251-757.
12. Amatoury J, Howitt L, Wheatley J, Avolio A, Amis T.
Snoring-related energy transmission to the carotid artery in rabbits.

J Appl Physiol 2006; 100:1547-53.

13. Rice T, Strollo P. Commentary on Jin-Cho et al.

Tissue vibration induces carotid artery endothelial dysfunction: a mechanism linking snoring and carotid atherosclerosis?

Sleep 2011; 34(6):251-757.

14. Guilleminault C, Huang Y, Kirisoglu C, Chan A.

Is obstructive sleep apnea syndrome a neurological disorder? A continuous positive airway pressure follow-up study.

Ann Neurol 2005; 58:880-7.

15. Dematteis M, Levy P, Pepin J-I.

A simple procedure for measuring pharyngeal sensitivity: a contribution to the diagnosis of sleep apnea.

Thorax 2005; 60:418-26.

16. Kimoff R J, Sforza E, Champagne V, Ofiara L, Gendron D.

Upper airway sensation in snoring and obstructive sleep apnea.

Am J Respir Crit Care Med 2001; 164:250-5.

17. Sabato R, Guido P, Resta S, Spanevello A, Barbaro F.

Airway inflammation in patients affected by obstructive sleep apnea.

Monaldi Arch Chest Dis 2006; 65:102-5.

Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Some embodiments may be distinguishable from the prior art for specifically lacking one or more features/elements/functionality (i.e., claims directed to such embodiments may include negative limitations).

The invention claimed is:

1. A system for assessing a patient, the system comprising:

a plurality of sensors, each sensor comprising a bipolar electrode, the plurality of sensors being configured for placement on a tissue surface of the patient and configured to produce signals responsive to at least EMG activity of at least one muscle proximate the tissue surface; and a probe comprising a flexible printed circuit board, wherein the plurality of sensors are arranged on the flexible printed circuit board in an array, the probe being configured with a size and shape to effect placement of the plurality of sensors in an oropharynx of the patient such that the plurality of sensors can detect EMG activity of the at least one muscle, the probe further comprising:

a proximal handle; and a distal curved body with a convex upper surface and a concave lower surface, and wherein the plurality of sensors are located on the convex upper surface and on the concave lower surface.

2. The system of claim 1, further comprising:

a processor having computer instructions operational therein configured for causing the processor to analyze signals from the plurality of sensors, and to determine whether the signals correspond to EMG activity of the at least one muscle;

wherein the computer instructions are additionally configured for causing the processor to differentiate EMG activity from EMG artifacts.

3. The system of claim 2, wherein the computer instructions are additionally configured to cause the processor to diagnose a condition of the patient based upon the determined EMG activity.

4. The system of claim 2, wherein the determined EMG activity corresponds to spontaneous EMG activity and/or abnormal MUP's of the at least one muscle.

5. The system of claim 2, wherein the tissue surface comprises mucosal tissue.

6. The system of claim 2, wherein the determined EMG activity corresponds to spontaneous EMG activity of the at least one muscle, comprising at least one of fibrillation potentials, positive sharp waves, complex repetitive discharges, fasciculation potentials, and myokymic discharges.

7. The system of claim 2, wherein one or more deviations from MUP benchmarks are selected from the group consisting of: area, size, shape, complexity, amplitude, duration, and phases of MUPs of the determined EMG activity.

8. The system of claim 2, wherein the computer instructions are additionally configured to cause the processor, upon a determination of EMG activity, to grade the determined EMG activity.

9. The system of claim 8, wherein grading comprises determining one or more periods of occurrence of the determined EMG activity.

10. The system according to claim 9, wherein the periods comprise at least one of rare, occasional, frequent and abundant.

11. The system of claim 1, wherein the probe further comprises a thermal sensor.

12. The system of claim 1, wherein at least one electrode of the plurality of sensors is spherical.

13. The system of claim 1, wherein each electrode of the plurality of sensors is spaced apart from an adjacent electrode by about 5 mm, or the spacing is configured to correspond to a muscle group in a posterior region of the mouth/pharynx area such that at least one electrode is positioned proximate a specific muscle or muscle layer.

14. The system of claim 11, wherein the thermal sensor is configured to output temperature signals corresponding to the temperature of at least one of a soft palate, pharyngeal wall and tongue of the oropharynx of the patient.

15. The system of claim 1, wherein the size and shape of the probe is configured such that at least one of the bipolar electrodes of the plurality of sensors contacts the tissue surface overlying at least one of the Levator Palatini, Tensor Palatine, Palatopharyngeus, Palatoglossus, Musculus Uvulae.

16. The system of claim 2, wherein the computer instructions are additionally configured to cause the processor to determine whether determined EMG activity comprises opposite side synchronization and symmetry of the EMG activity of at least a palate in the oropharynx of the patient, and comparing the EMG activity with that of EMG activity of a non-apnea patient.

17. The system of claim 1, wherein each sensor of the plurality of sensors comprises a domed shape protruding from the convex upper surface or concave lower surface.

18. The system of claim 1, wherein the size and shape of the probe is configured such that at least one of the bipolar electrodes of the plurality of sensors contacts the tissue surface overlying at least one muscle of a soft palate, a lateral pharyngeal wall, and a tongue.

19. The system of claim 1, wherein the probe further comprises at least one probe marking proximal to the plurality of sensors.

20. The system of claim 1, wherein a greater number of the plurality of sensors is located on the convex upper surface than the concave lower surface.

21. The system of claim 1, wherein the plurality of sensors located on the concave lower surface are located on a distalmost region of the distal curved body.

* * * * *